United States Patent [19]
Rosen et al.

[11] Patent Number: 5,462,255
[45] Date of Patent: Oct. 31, 1995

[54] AUTOMATIC FLUID CONTROL VALVE

[75] Inventors: Jonathan J. Rosen, Alpharetta; Charles E. Larsen, Cumming, both of Ga.

[73] Assignee: Novoste Corporation, Norcross, Ga.

[21] Appl. No.: 217,672

[22] Filed: Mar. 25, 1994

Related U.S. Application Data

[63] Continuation-in-part of Ser. No. 154,944, Nov. 19, 1993.
[51] Int. Cl.⁶ ..................................................... F16L 37/28
[52] U.S. Cl. ..................................... 251/149.6; 251/149.1
[58] Field of Search ............................. 251/149.1, 149.6; 604/249, 905

[56] References Cited

U.S. PATENT DOCUMENTS

| | | | |
|---|---|---|---|
| 2,832,338 | 10/1954 | Ryan | 128/214 |
| 3,861,388 | 1/1975 | Vaughn | 128/214 R |
| 4,112,944 | 9/1978 | Williams | 128/346 |
| 4,332,369 | 6/1982 | Gordon et al. | 251/114 |
| 4,432,767 | 2/1984 | Lobdell et al. | 604/86 |
| 4,535,820 | 8/1985 | Raines | 137/854 |
| 4,834,716 | 5/1989 | Ogle, II | 604/192 |
| 4,878,897 | 11/1989 | Katzin | 604/86 |
| 4,915,687 | 4/1990 | Sivert | 604/83 |
| 4,946,445 | 8/1990 | Lynn | 604/192 |
| 5,046,645 | 9/1991 | Hagan et al. | 251/149.6 |
| 5,061,253 | 10/1991 | Yoshida | 604/246 |
| 5,139,483 | 8/1992 | Ryan | 604/905 |
| 5,163,922 | 11/1992 | McElveen, Jr. et al. | 604/249 |
| 5,203,775 | 4/1993 | Frank et al. | 604/256 |
| 5,215,538 | 6/1993 | Larkin | 251/149.1 |
| 5,226,898 | 7/1993 | Gross | 604/243 |
| 5,242,432 | 9/1993 | DeFrank | 604/284 |
| 5,279,571 | 1/1994 | Larkin | 604/167 |
| 5,281,206 | 1/1994 | Lopez | 604/283 |
| 5,289,849 | 3/1994 | Paradiss | 251/149.1 |
| 5,360,413 | 11/1994 | Leason et al. | 604/249 |

*Primary Examiner*—A. Michael Chambers
*Attorney, Agent, or Firm*—Bernstein & Associates

[57] ABSTRACT

A fluid control valve assembly including a first tube member, a second tube member and a cylindrical valve element. The first tube member has a narrower diameter passageway connected by a transitional surface to a wider diameter passageway. The narrower passageway acts as a secondary valve sealing surface and the transitional surface acts as a primary valve sealing surface. The valve element includes a primary valve sealing shoulder which forms a seal when in contact with the primary sealing surface of the first tube member; at least one secondary sealing flange which deformingly engages the wall of the narrower passageway; and a plurality of elastomeric bands extending from the base of the valve element. The bands are looped around posts extending upward from the inner wall of the second tube member when the valve assembly is assembled. The elastic bands maintain the valve element in a compressively engaged sealing relationship with the transitional surface of the first tube member. The valve element is urged partially downward when a connector is fitted onto the first tube member, breaking the primary seal. When the connector is in a fully locked position, the secondary seal is broken, permitting fluid flow in either direction. When the connector is removed, the elastic bands urge the valve element upward reforming the seals.

34 Claims, 10 Drawing Sheets

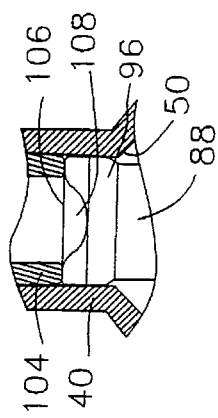
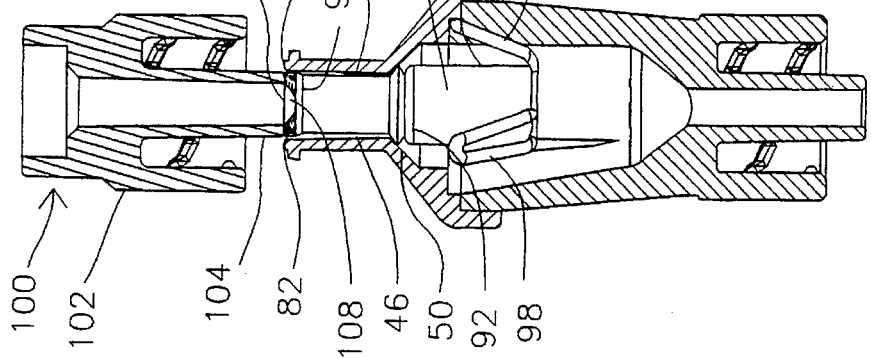
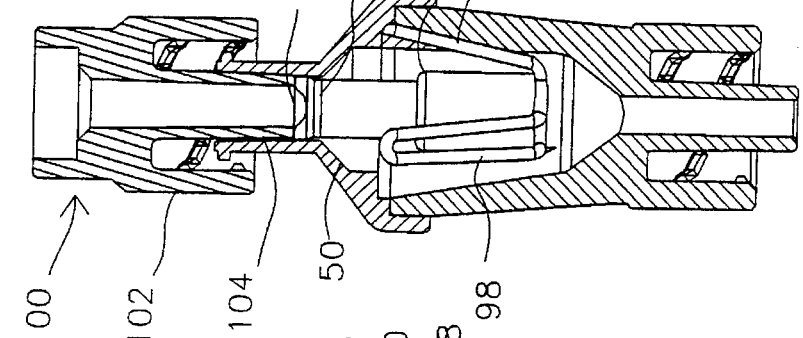
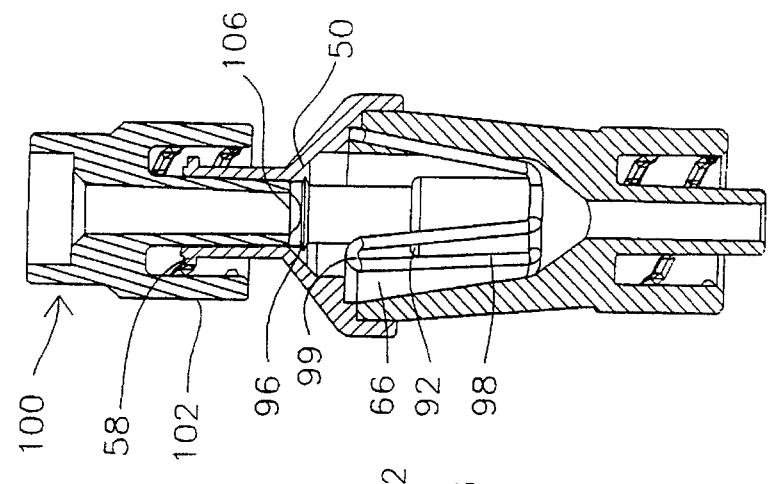

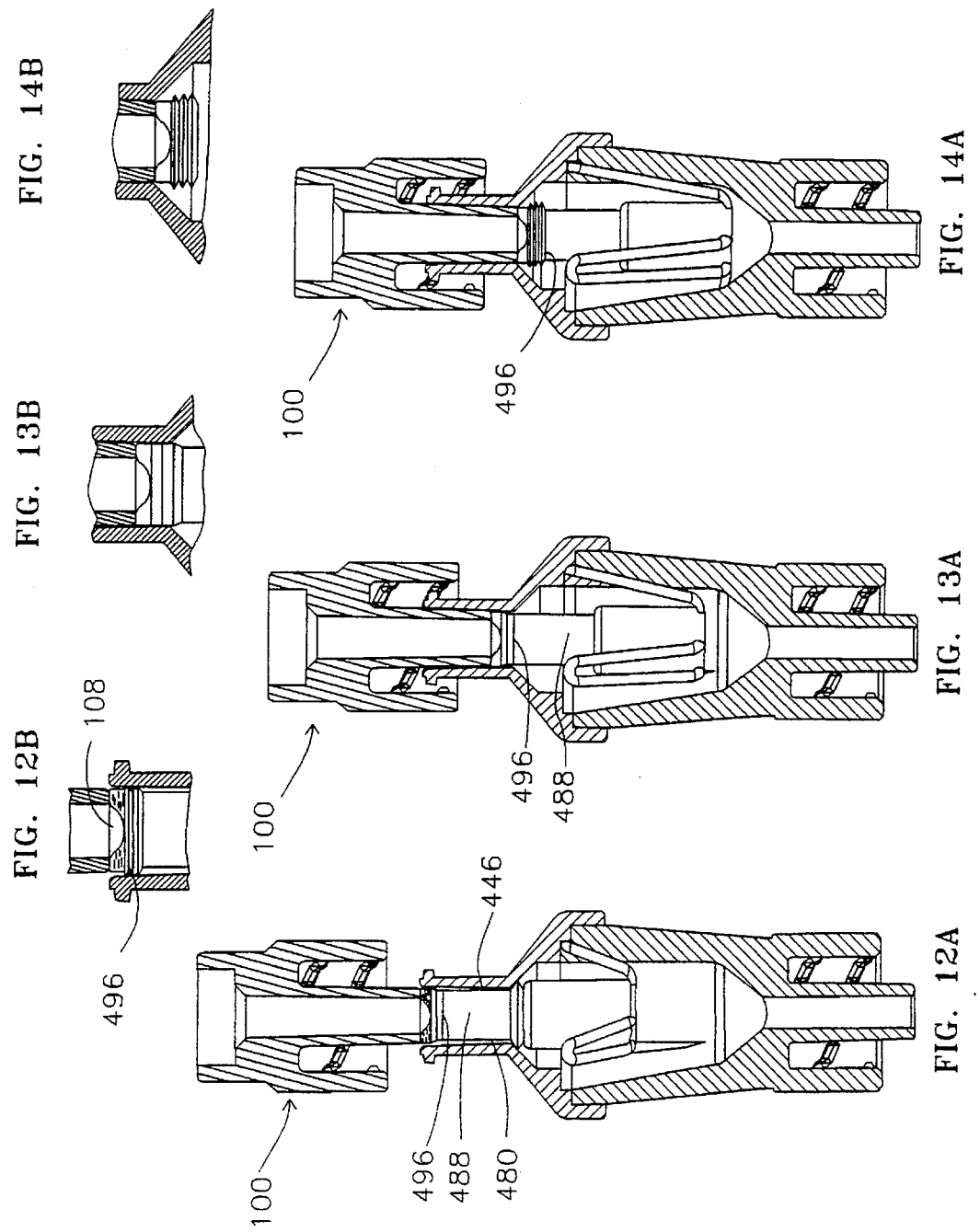

AUTOMATIC FLUID CONTROL VALVE

CROSS-REFERENCE TO RELATED APPLICATION

This application is a continuation-in-part of application Ser. No. 08/154,944, filed Nov. 19, 1993, which is incorporated by reference herein in its entirety.

FIELD OF THE INVENTION

The present invention relates to a fluid control valve, and more particularly to an automatic valve having a valve element maintained in elastically sealing engagement with a tube member.

BACKGROUND OF THE INVENTION

Flow control valves for liquid and gas come in many shapes and sizes, and are made of a wide variety of materials depending on their intended use.

Typically, flow control valves such as butterfly valves and gate valves are used to control flow of fluid by moving a mechanical member into and out of the flow path to partially or completely block the flow path. Other types of valves, for example roller clamps used in medical intravenous apparatus, control flow by pinching the plastic tubing through which the fluid flows. Still other types of valves operate by controlling the length of the flow path, and therefore the resistance to flow, through the valve.

Despite the wide variety of valves that have been used heretofore, there is a continuing need for improved flow control valves that have cost, ease of use, functional, and other advantages compared to prior flow control valves. A significant need exists for a valve that contains a minimum number of parts, and that those parts form a sealed access port which can be effectively cleaned by an alcohol wipe.

DESCRIPTION OF THE PRIOR ART

U.S. Pat. No. 5,215,538, issued to Larkin discloses an in-line valve having a mated pair of tube members and a valve member comprising an elastomeric membrane having flow holes therein and a projection extending from the membrane. The membrane is secured across the passageway between the two tube members by a rim which engages the ends of the tube members when mated. The membrane is "tensioned across and in sealing engagement with the annular valve seat." The projection is urged downward when a connector engages the projection and the valve seal is broken, permitting fluid flow.

The inlet tube of Larkin must be of a certain minimum depth to engage and lock with a standard luer taper connector. The projection associated with the valve membrane is inserted during assembly into the inlet tube. Even with full insertion there remains an empty well that is exposed to the air and which can collect dirt and contaminants. This well cannot easily be cleaned. If the projection were modified to be long enough to fill the inlet tube, when a connector was inserted the amount of downward displacement of the projection would likely cause the valve membrane to rupture. Therefore is not likely that Larkin could be adapted to remedy this deficiency.

Larkin utilizes a valve member in which the sealing surface is also the elastomeric member. In other words, the seal itself must stretch both laterally and axially. A problem with this type of design is that the deformation of the valve seal may not be even when the projection is moved downward to break the seal, resulting in possible fluid leakage around the membrane. Furthermore, the elastomeric membrane cannot be deformed axially significantly if it is to maintain the valve seal. It would be desirable to have a valve seal that does not require lateral deformation so as to ensure a proper fluid tight seal.

In Larkin, once the luer connector moves the projection downward even partially the valve seal is broken. Until the connector is locked into place there exists the possibility of fluid leakage back through the seal and the luer taper inlet tube to the inlet connector because there is no secondary seal anticipated that is maintained until the connector is locked in place. Where there is substantial back pressure this may result in contamination of the inlet fluid.

It would be desirable, then, to have a fluid control valve which would utilize a valve that is held in displaceable sealing engagement with a valve sealing surface and that would in a closed position completely fill the connector passageway so as to form a seal that would be cleanable by an alcohol wipe.

SUMMARY OF THE INVENTION

The present invention provides a fluid control valve assembly including a first tube member having an inner wall forming a first and second passageways, the passageways being connected by a transitional wall portion, a second tube member and a cylindrical valve element. The valve element includes a primary valve seal comprising a shaped shoulder which forms a seal when in contact with the transitional wall portion of the first tube member, a secondary valve seal comprising at least one flange which deformingly engages the first passageway of the first tube, and a plurality of elastomeric bands extending from the base of the valve element. The bands are looped around posts extending upwardly from the inner wall of the second tube member when the valve assembly members are assembled. The elastic bands are maintained in tensioned deformation and place an upward force on the valve element which maintains the valve element in a compressively engaged sealing relationship with the transitional portion of the inner wall of first tube member.

When a suitable luer type male connector is fitted onto the first tube member the valve element is urged downward causing separation of the shoulder and the primary valve sealing surface. Until the flange clears the first passageway fluid is prevented from passing beyond the flange into the second passageway. When the connector is locked into place the secondary seal is broken and fluid can pass in either direction through the valve assembly. When the connector is removed, the elastic bands urge the valve element upward, reforming the seals.

In a preferred embodiment, the present invention provides a fluid control valve, comprising a first tube member having a first portion defining a first passageway having a tapered diameter and a second portion defining a second passageway having a diameter greater than the first passageway, a transitional inner surface between the first and second passageways defining a valve sealing surface; a second tube member having an inner passageway defined therein and a top end and bottom end, the first and second tube members capable of mating engagement with axial alignment; a cylindrical valve element having an upper portion terminating in a top surface and a lower portion, the lower portion having a larger diameter than the upper portion, the junction between the upper and lower portions defining a shaped shoulder; at least one deformable beveled annular flange disposed circumferentially about the upper portion of the valve seal member capable of sealingly engaging the first passageway to form a secondary valve seal so as to prevent fluid from passing therebetween; a plurality of elastic members, each member comprising a segment of an elastomeric material, each end of the elastomeric material being associated with the lower portion of the valve seal member so as to form a loop; means associated with the second tube member for retaining the plurality of loops comprising a plurality of posts extending from the inner wall of the inner passageway, whereby the elastic members are capable of compressing the valve element shoulder in tensioned engagement against the valve sealing surface to form a primary valve seal; means associated with the top surface of the upper portion for forming a fluid passageway between the top surface and a male luer connector capable of engaging the first tube member, the means comprising at least one projection extending from the top surface, whereby when the connector engages the top surface and is forced downward and locked in place, the valve element shoulder is urged downward against the tension created by the elastic members, thereby first releasing the primary valve seal and then releasing the secondary valve seal and permitting passage of fluid therethrough and when the connector is disengaged from the top surface, the seals are reformed and the top surface is generally even with the top end of the first tube member.

The elastic members provide an even tension to the valve element and assist in maintaining the valve element in a centered position within the first and second tube members.

The valve element can be molded of a softer deformable material and the rigid top surface component can be molded of a harder material which will not substantially deform when contacted by the connector.

In an alternative embodiment, the secondary valve seal comprises a plurality of flanges circumferentially spaced along the axis of the valve element about the upper portion. The plurality of flanges creates a more leakproof secondary seal within the valve assembly.

In an other alternative embodiment, the top surface of the valve element is a separate component that comprises a stud and a disk like cap. The stud is sized to be received within an axial bore extending partially into the upper portion of the valve element.

The valve assembly of the present invention can be adapted to be connected to a number of different devices, such as but not limited to, a male luer fitting, a manifold, a tube, and a Y-site tube.

Accordingly, it is a principal object of the present invention to provide an automatic fluid control valve having a minimal number of parts.

It is a further object of the present invention to provide a valve that forms a sealed access port which is externally cleanable with an alcohol wipe.

It is another object of the present invention to provide a valve having a seal maintained by separate elastic members associated with the valve.

It is a further object of the present invention to provide a valve having a valve sealing portion that is independent of the elastomeric tensioned portion.

It is another object of the present invention to provide a tensioned releasable seal between a valve shoulder member and a passageway such that the elastic members are stretched to maintain the seal.

It is yet another object of the present invention to provide a valve having an automatic positive seal in the closed position to prevent leakage of fluids in both directions.

It is still another object of the present invention to provide a valve having a secondary seal comprising one or more annular flanges to prevent contamination of the inner parts of the valve and to prevent back flow of fluids.

It is a further object of the present invention to provide a valve capable of maintaining a fluid tight seal while a standard luer connector is being attached to the valve and minimizing the possibility of back flow leakage.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures of which:

FIG. 5 is a side elevational view in partial cutaway of the valve assembly in a closed position with a male luer connector.

FIG. 6 is a side elevational view in partial cutaway of the valve assembly with the valve element being moved partially downward by partial engagement with a male luer connector.

FIG. 7 is a detail of the flange and top surface of the valve element and the tip of the male luer connector.

FIG. 8 is a side elevational view in partial cutaway of the valve assembly with the valve element being in an open position with locking engagement with a male luer connector.

FIG. 12A is a side elevational view in partial cutaway of an alternative embodiment of the valve element having a plurality of flanges, with the valve assembly in a closed position with a male luer connector.

FIG. 12B is a detail of the flanges and top surface of the valve element and the tip of the male luer connector.

FIG. 13A is a side elevational view in partial cutaway of the valve assembly with the valve element being moved partially downward by partial engagement with a male luer connector.

FIG. 13B is a detail of the flanges and top surface of the valve element and the tip of the male luer connector.

FIG. 14A is a side elevational view in partial cutaway of the valve assembly with the valve element being in an open position with locking engagement with a male luer connector.

FIG. 14B is a detail of the flanges and top surface of the valve element and the tip of the male luer connector.

DESCRIPTION OF THE PREFERRED EMBODIMENTS

Figure 1:
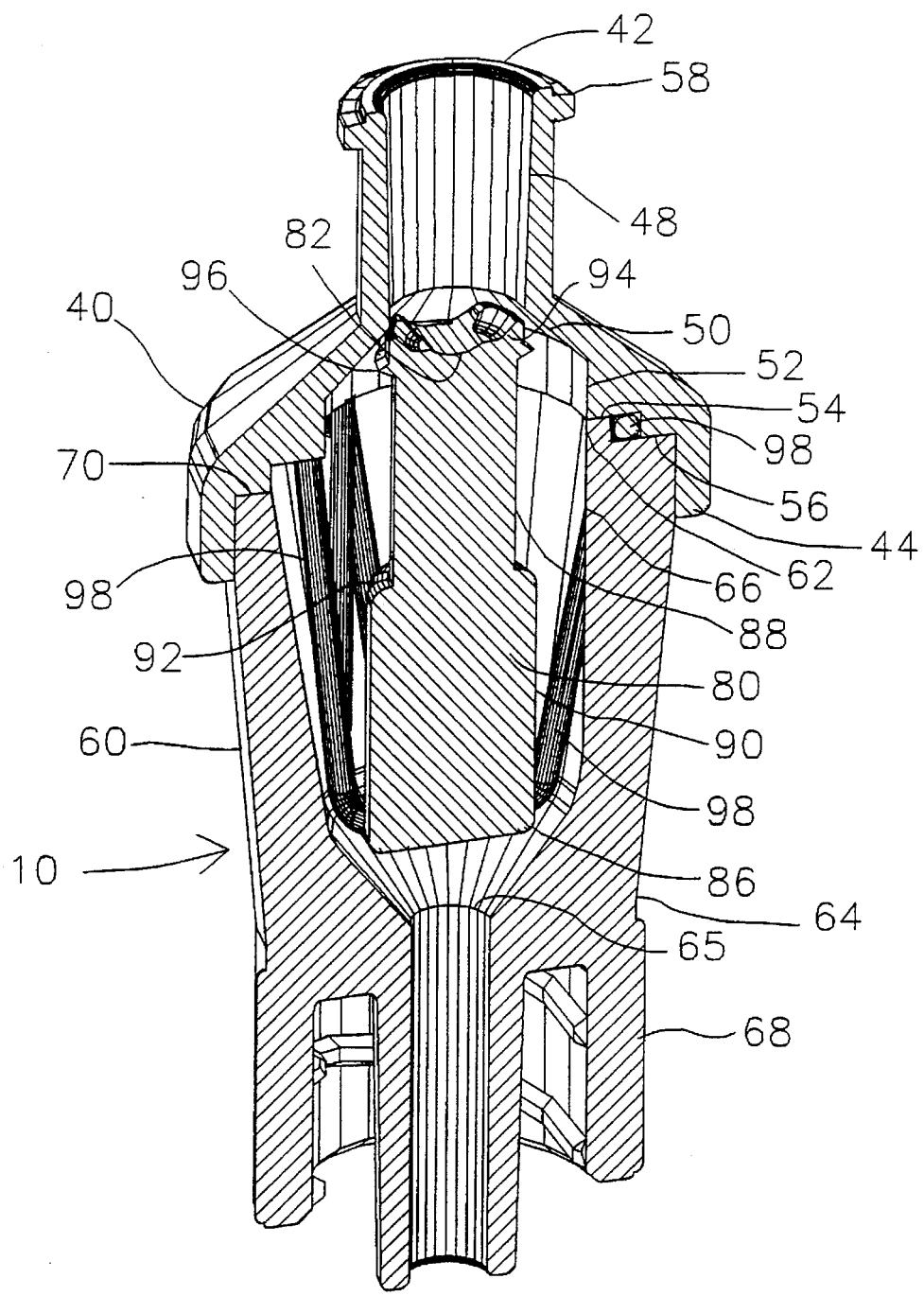
FIG. 1 is a perspective view in cutaway of a preferred embodiment of the present invention.

As illustrated in FIG. 1, a valve assembly 10 consists generally of a two part body member 20 comprising a first tube member 40, a second tube member 60 and a valve element 80 slidingly disposed within the body. The first and second tube members 40 and 60 are made of a rigid material, such as a polymeric or plastic material. Other materials can be used, such as metal or ceramic, but a polymeric material such as carbonate, acrylate, or other solvent resistant moldable material is preferred. For the purposes of the present disclosure the terms top, bottom, up and down, and the like, are used merely for convenience, and not limitation, when viewing the drawings with the first tube member 40 being positioned over the second tube member 60.

The first tube member 40 comprises a cylindrical housing having a first end 42 and a second end 44. A tapered luer bore extends through a portion of the first end 42 forming a first passageway 46. The inner wall 48 of the first passageway 46 functions as a secondary valve sealing surface. A transitional portion of the bore of the first tube member 40 widens gradually forming a primary valve sealing surface 50. A further portion of the bore continues partially toward the second end 44 forming a second passageway 52 having a larger diameter than the first passageway 46. A pair of ledges 54 and 56 are formed by successive widenings of the second passageway diameter. An external thread 58 projects outwardly from the circumference just below the first end 42, and is sized to be capable of mating with a male luer fitting.

Figure 2:
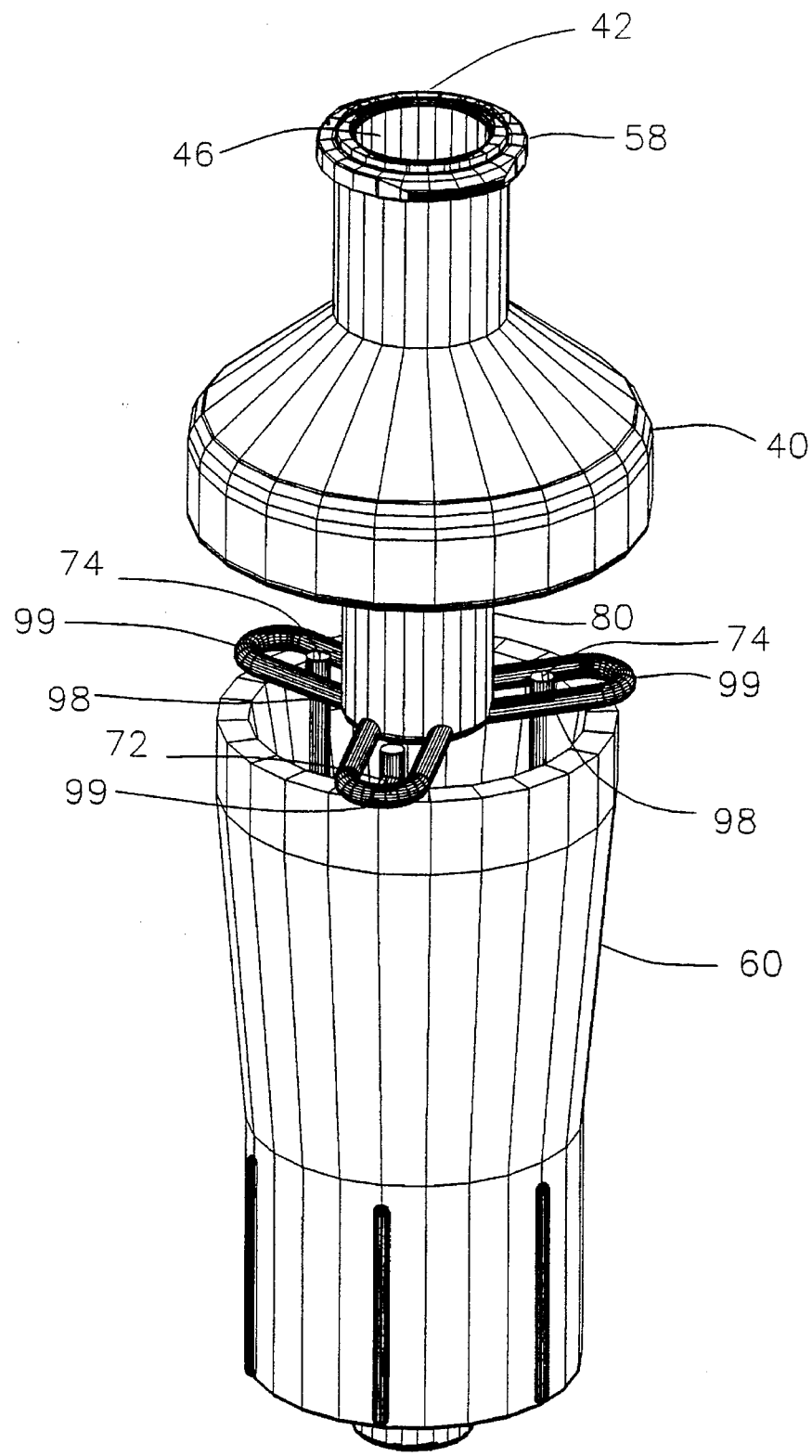
FIG. 2 is a perspective view of the main components of the valve assembly aligned for engagement.

The second tube member 60 comprises a cylindrical housing having a first end 62 and a second end 64 with a bore extending therethrough defining a passageway 66 having a diameter substantially the same as the diameter of the second passageway 52. This diameter preferably tapers slightly toward the second end 64. The second end 64 has an opening 65 and can optionally have a male luer fitting 68 associated therewith and fluid communication with the passageway 46. The male luer fitting 68 can be connected to an external thread on a separate connector. Alternatively, the second end 64 can be adapted to be fitted to a tubing in a Y-site configuration, or other configurations, as described in detail hereinbelow. The first end 62 has a rim 70. A plurality of extensions 72 each project generally outward from the wall of the inner passageway 66, and terminate at the upper end in a post 74, as shown in FIG. 2. The posts 74 extend slightly above the rim 70.

The valve element 80 comprises a resilient deformable cylinder having a top surface 82, a bottom end 86, an upper portion 88 and a lower portion 90. The lower portion 90 has a larger diameter than the upper portion 88, with a shaped shoulder 92 being defined between the upper and lower portions, generally midway between the top surface 82 and the bottom end 86. The shoulder 92 is preferably deformable so as to form a releasable fluid tight seal with the primary valve sealing surface 50. The valve element 80 is sized to permit the upper portion 88 to be slidingly receivable within the first passageway 46.

Figure 3:
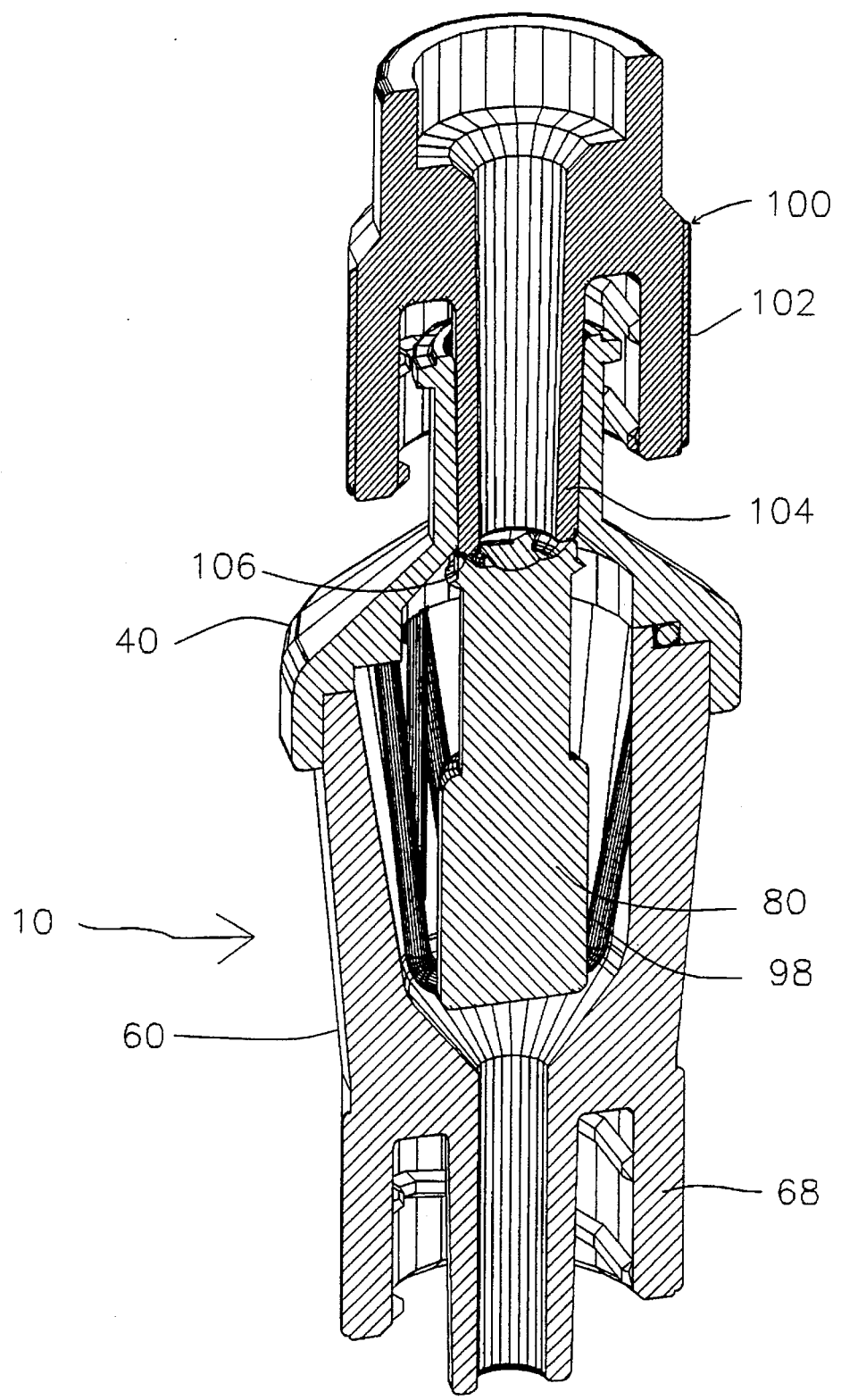
FIG. 3 is a perspective view in cutaway including a male luer connector.

The top surface 82 has at least one projection 94 extending upward. The projection 94 can take any of a number of possible forms, such as, but not limited to, ridges, bumps, shapes such as a cross, triangle, parallel lines, cross-hatching, and the like. Essentially any suitable shape or arrangement of projections is usable which prevent formation of a fluid tight seal between the top surface 82 and a connector tube 100, as will be discussed in detail hereinbelow. A preferred embodiment is shown in FIG. 3, in which the projection 94 comprises a pair of ridges sloping toward the center.

In a preferred embodiment, a deformable beveled flange 96 projects annularly from the upper portion 88 and is sized to form a fluid tight seal with the secondary tapered valve sealing surface 48 when the upper valve element portion 88 is slidingly received within the first passageway 46.

Figure 4:
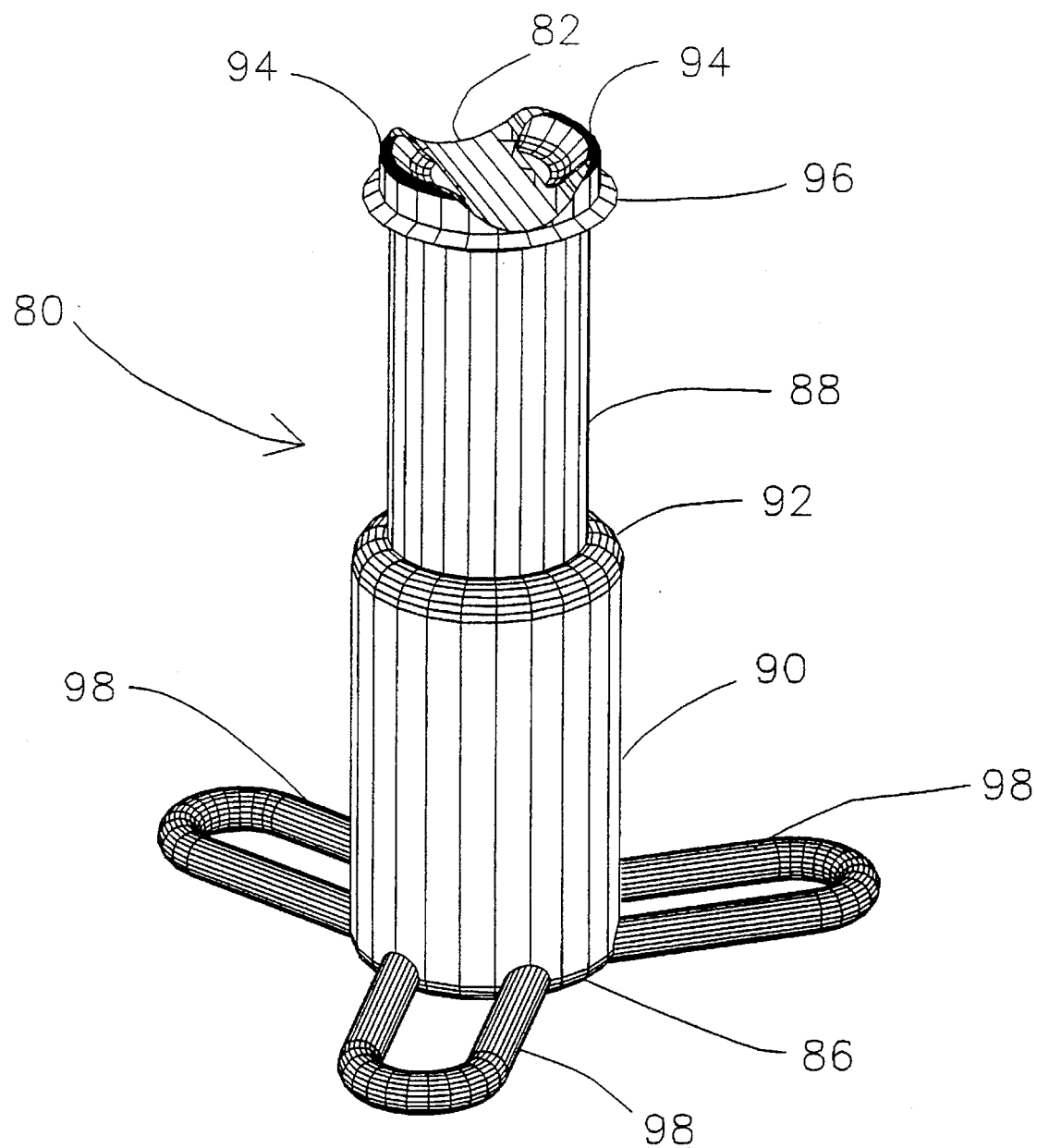
FIG. 4 is a detail of the valve element of the preferred embodiment of the present invention.

A plurality of elastic bands 98 extend from the lower portion 86, as shown in FIG. 4. In a preferred embodiment, the bands 98 are formed as part of the valve element 80 during the molding process; however, other conventional means for attachment, such as glue, sonic or heat welding, and the like, are possible. The bands 98 are formed of an elastomeric material and are capable of substantial elongation, up to several times their undeformed length. Each band 98 forms a loop 99, which can fit over the post 74. The bands 98 are equidistantly spaced around the circumference to provide substantially equal tension to the valve element 80. This equal tensioning also centers the valve element 80 within the passageway 66 and ensures a uniform seal by the shoulder 92 against the primary valve sealing surface 50.

The second end 44 of the first tube member 40 can be frictionally engaged to the first end 62 of the second tube member and sealed by conventional means, such as but not limited to solvent, glue, sonic or heat sealing, fusing, and the like. It is preferable that when the two tube members are connected they form fluid tight seal, yet can permit fluid to pass through the passageways when the primary and secondary valve seals are released. When the two tubes members are aligned for connection as shown in FIG. 2, the elastic bands 98 are positioned over the posts 74. When the two tube members are mated the rim 70 mates with the ledge 56 and the loops 99 are prevented from slipping off of the posts 74. Additionally, the bands 98 are stretched slightly by the valve element 80 exerting a downward force on the bands 98 to place an upward force on the valve element 80, maintaining the valve element 80 in pre-tensioned engagement with the primary valve sealing surface 50.

FIGS. 5–8 show the valve element 80 in three positions with respect to the first and second tube members. FIG. 5 shows the valve element in the closed position. In this position the valve element 80 substantially fills the secondary valve sealing surface 48 and top surface 82 is generally even with the opening at the first end 42 of the first tube member. The flange 96 provides a fluid tight secondary seal with the secondary valve sealing surface 48 by being slightly deformed and compressed against the surface, preventing contaminants from entering the valve assembly 10. This novel feature provides a more cleanable valve assembly and reduces the risk of introducing contaminants during valve operation. In this closed position the shoulder 92 is maintained in compressive engagement with the primary valve sealing surface 50 by the upward tension of the bands 98, thus forming the primary valve seal. The amount of upward force provide by the elastic bands 98 is sufficient to overcome any normal back fluid pressure which might otherwise cause fluid leakage in the valve assembly 10. The combination of the primary valve seal and the secondary valve seal aid significantly in providing an improved sealing function of the valve assembly 10.

When a male luer connector 100 having a fitting 102 is partially inserted by a user into the first end 42 of the first tube member 40, as shown in FIGS. 6 and 7, the end 104 of the fitting 102 contacts the top surface 82 and the projection 94 and the tip 106 enters the first passageway 46. The projection 94 forms fluid passageways 108 with the tip 106 to permit fluid to pass from the connector 100 into the first passageway 46, but is blocked from communication with the second passageway by the flange 96. As the tip 106 is urged downward into the first passageway 46, and until the flange 96 clears the first passageway 46 and the uppermost portion of the primary valve sealing surface 50, the flange 96 maintains a fluid tight secondary seal with the first passageway 46. The flange 96 deforms slightly more as the valve element 80 moves downward and the first passageway 46 tapers, as shown in FIG. 7. When the valve element 80 is initially urged downward, the shoulder 92 moves downward away from the primary valve sealing surface 50, thereby breaking the primary valve seal. The flange 96 moves downward within the first passageway 46 while the connector tip 106 moves downward and the flange 96 provides a continuous confirming seal until the connector 100 is locked into place over the first end 42. During this downward movement, the elastic bands 98 elongate in response to the downward force placed on the valve element 80 by the tip 106. Fluid can pass between the primary seal elements (the shoulder 92 and the secondary valve sealing surface 50), but is prevented by the secondary valve seal (the flange 96 and the secondary valve sealing surface 48) from communicating with the tip 106.

FIG. 8 shows the valve element 80 in the down or open position wherein the top surface 82 and the flange 96 have cleared the first passageway 46 and the uppermost portion of the primary valve sealing surface 50, breaking the secondary valve seal and permitting passage of fluid from the tip 106 through the first passageway 46 and the second passageway 66. Fluid urged into the tip 106 through the male luer connector 100 can pass through the valve assembly 10 and out the second end opening 65 or in the reverse direction, if desired, such as when the connector 100 is part of a syringe which can withdraw fluid from a Y-site tube connected to the bottom end 64. In this position the connector 100 is connected to the valve assembly 10 by the male luer fitting 102 threadingly engaging the rim 58 in a manner well known to those skilled in the art.

Upon removal of the connector 100, the elastic bands 98 contract and urge the valve element 80 back upward into the closed position, thus reforming the primary and secondary valve seals and preventing passage of fluids through the valve assembly 10.

The valve element 80 is preferably made of an elastomeric material such as silicone rubber, polyurethane or a suitable copolymer. In an alternative embodiment the valve element 80 can be made of a material having two or more different density areas. In this embodiment the top surface 82, preferably including the upper portion 88, is of a higher durometer material and is less deformable. The projections 94 will not deform substantially, thus ensuring adequate fluid passageways through which fluid can pass. The shoulder 92 and area thereabout can be made of a lower density that is more deformable, thus ensuring a fluid tight seal when engaging the primary valve sealing surface 50.

Figures 9A, 9B:
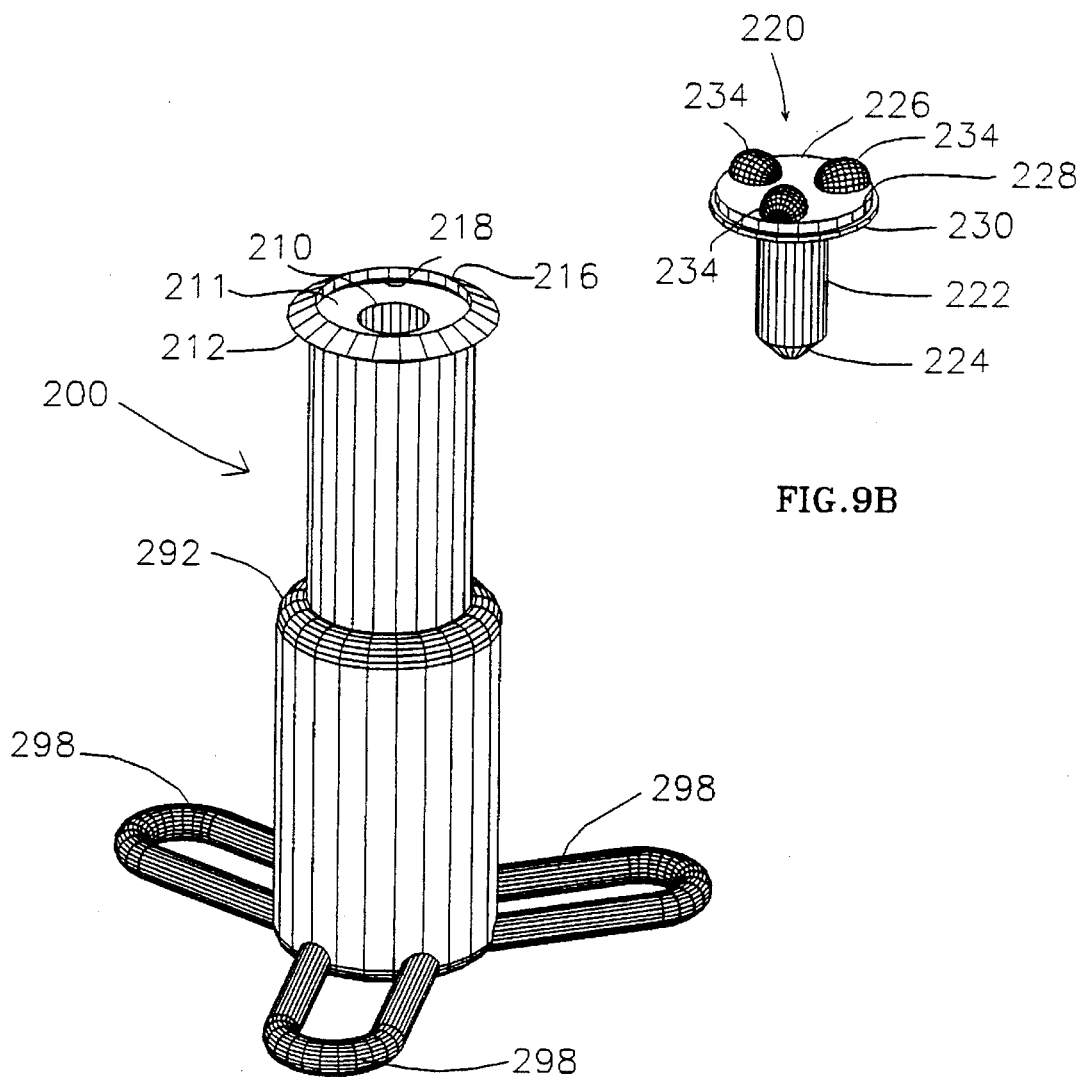
FIG. 9A is a perspective view of an alternative embodiment of the valve element.
FIG. 9B is a perspective view of a first embodiment of the valve element cap.

In an alternative embodiment of the present invention shown in FIGS. 9A and B, the shape and design of a valve element 200 is substantially the same as valve element 80 of the preferred embodiment with the following distinctions. A bore 210 extends from a surface 211 axially through a portion of the valve element 200. A flange 212 extends circumferentially from the outer wall of the upper portion of the valve element 200, similar to the valve element 80. The top surface 211 comprises a generally flat surface, above which is an inwardly tapering lip 216, which creates an annular undercut slot 218 by forming a tight seal.

A cap 220 comprises an annular stud 222 which is sized to be received within the bore 210. Preferably the stud 222 terminates at its lower end in a taper 224 to facilitate insertion into the bore 210. A generally flat circular disk 226 extends from the top end of the stud 222. The disk 226 has a rim 228 around which is a ledge 230 having a diameter greater than that of the disk 226. At least one, and preferably a plurality of, bumps 234 project from the top surface 232. These bumps 234 function in a manner similar to the projections 94 of the preferred embodiment, i.e., to provide fluid passageways when a connector (not shown, but is similar to the connector discussed in the preferred embodiment) is contacted against and urged downward on the bumps 234.

Figure 11:
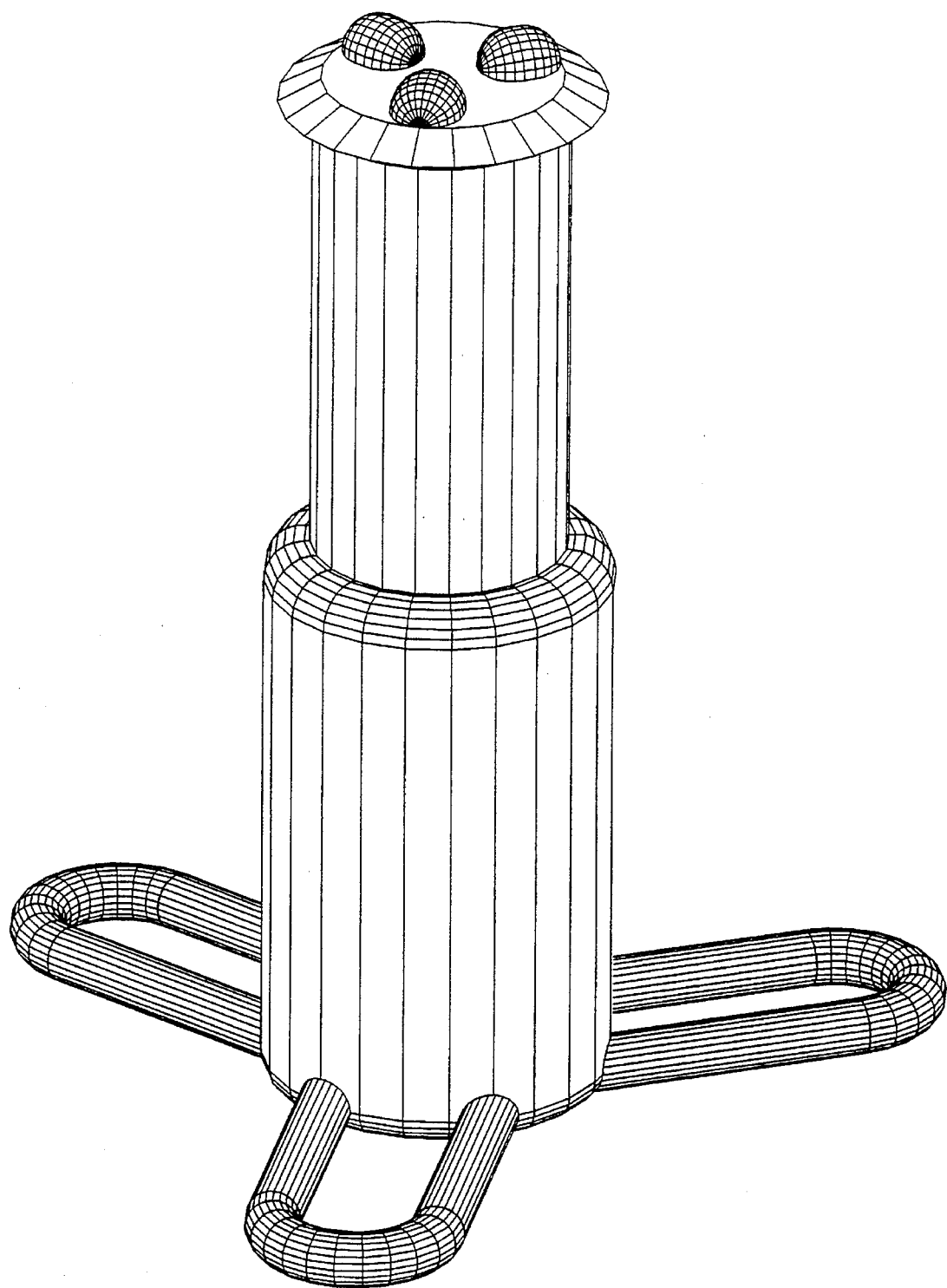
FIG. 11 is a perspective view of the valve element with the cap fully inserted into the valve element.

During assembly of the valve of this embodiment, the stud 222 is inserted into the bore 210 and the ledge 230 is frictionally forced down over the lip 216 and is maintained with the slot 218 by the lip. The lip 216 also prevents contaminants from entering the bore 210 or the slot 218. FIG. 11 shows the cap 220 after insertion into the bore 210.

In this alternative embodiment, the valve element 200 is preferably molded or out of a uniform density deformable material which provides deformability to the shoulder 292 and elasticity to the elastic members 298. The cap 220 can be molded or otherwise manufactured out of a harder, less deformable material so that when the connector is contacted with the bumps 234 the bumps to not compress and close the fluid passageways.

Figures 10A, 10B:
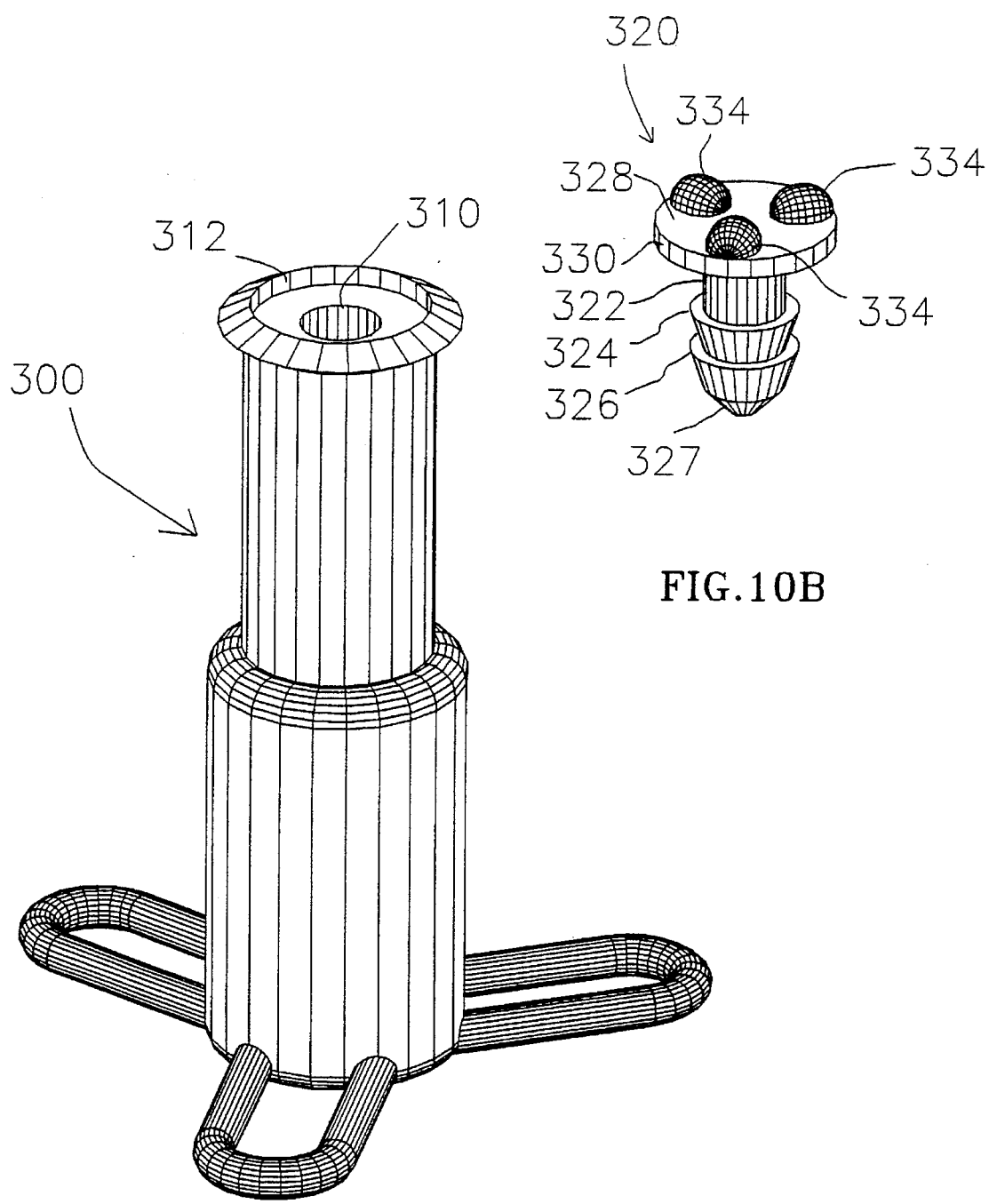
FIG. 10A is a perspective view of a second alternative embodiment of the valve element.
FIG. 10B is a perspective view of a second embodiment of the valve element cap.

In a further alternative embodiment, shown in FIGS. 10A and B, the valve element 300 is similar to the valve element 200 in design and material except that it does not have the undercut slot 218; rather it has a straight sided lip 312. A cap 320 has a stud 322 having a series of barbs 324 and 326 (any number of barbs is possible) and a tapered tip 327. A disk 328 has a rim 330, but no ledge. The bumps 334 are substantially the same as the bumps 224. In this embodiment the cap 320 is constructed of a material of similar properties as the cap 220, for the same reasons. In assembly of this embodiment, the stud 322 is inserted into a bore 310 and retained within the deformable bore by the barbs 324 and 326 by a frictional fit, as shown in FIG. 11. It is to be understood that other configurations of the cap 320 and the shape and arrangement of the bumps are possible and within the scope of the present invention.

In yet a further alternative embodiment, shown in FIGS. 12-14, the upper portion 488 of the valve element 480 includes a plurality of deformable beveled flanges 496 that enhance the secondary valve seal (as shown in detail in FIG. 12A). The flanges 496 deform as the valve element 480 is urged downward by the connector 100 (as shown in detail in FIG. 13A) and, as the flanges pass beyond the first passageway 446, they spring back to their beveled shape (as shown in detail in FIG. 14A).

Figure 15:
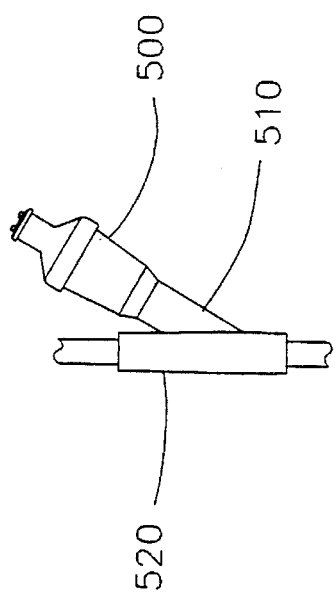
FIG. 15 is a side elevational view of an alternative embodiment where the valve assembly is connected to a Y-site tube.
Figure 17:
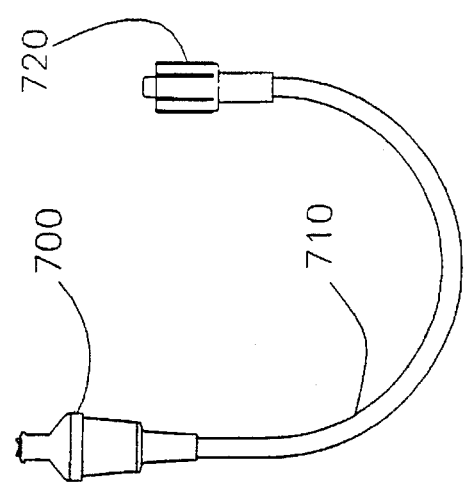
FIG. 17 is a side elevational view of an alternative embodiment where the valve assembly is connected to a tube.
Figure 16:
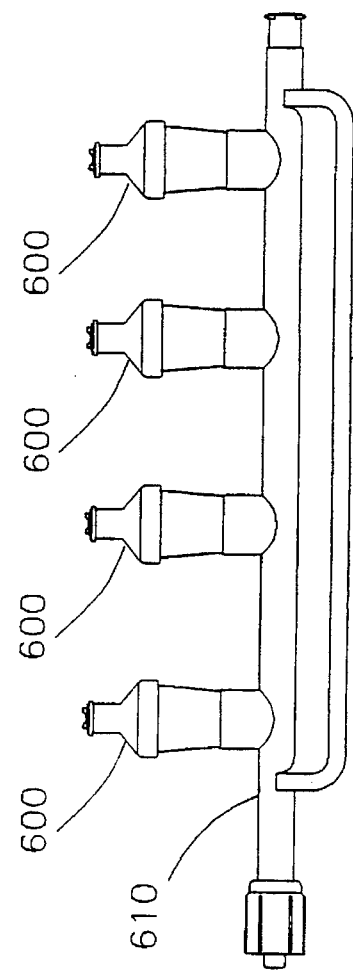
FIG. 16 is a side elevational view of an alternative embodiment where a plurality of the valve assemblies are connected to a braced manifold.

The valve assembly of the present invention can be adapted to be connected or part of various connector configurations, as illustrated in FIGS. 15–17. In each configuration the male luer fitting 68 of the preferred embodiment has been replaced by an alternative connection. FIG. 15 illustrates a valve assembly 500 connected to a tube 510 that is in fluid connection with a main tube 520, the configuration commonly being known as a Y-site connection. FIG. 16 illustrates a four-valve manifold and brace assembly having a number of valve assemblies 600 connected in series to a common manifold 610. A brace 620 maintains the manifold 610 in a stable alignment. FIG. 17 illustrates a valve assembly 700 connected to a tube 7 10 which terminates in a male luer fitting 720. It is to be understood that other connection configurations are contemplated as within the scope of the present invention.

An advantage of the present invention is that the combination of the primary and secondary valve seals reduce the likelihood of fluid leakage. The stretching force of the elastic bands 98 provides a positive compressive primary seal by the shoulder 92 against the surface 50 and the flange 96 against the first passageway 46 provides a positive secondary seal. Since the flange 96 maintains its seal whether stationary or when the valve element 80 is moving up or down within the first passageway 46, no fluid can leak through in either direction. Prior art devices that do not fill the tapered passageway with the valve element have a well created within the first passageway which can collect dirt and contaminants and possibly leak. An advantage of the present invention is that the flange 96 seals the first passageway 46 even though the passageway tapers. If the upper portion 88 of the valve element 80 were completely rigid, it could not form an adequate seal as the passageway narrows. The deformable flange 96 maintains this seal.

An additional advantage of the present invention is the novel use of the elastic bands 98. The bands can stretch up to several times their original length, allowing the design of the valve element to be such that the top surface 82 is even with the top of the first end 42. The separation of the elastomeric element (the bands 98) from the sealing element (the shoulder 92) provides substantially increased flexibility in designing the valve element. Greater movement is possible than with previous valve designs which have the elastomeric element as part of the sealing element; thus, the first passageway 46, which, as part of a standard luer design, must be of a certain minimum length, is effectively sealed by the upper portion 88 and flange 96 of the present invention when the elastic bands 98 are stretched.

The present invention substantially eliminates the undesirable well present in other designs that may require separate caps to prevent contamination of the well.

The present invention also minimizes the number of parts required to function properly and be cost effective. Moreover, as the fittings on both ends of the assembly 10 are conventional luer or other connections, use is intuitive and no special training or instructions are necessary.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

I claim:

1. An automatic fluid control valve, comprising:

a first rigid tube member having a top and a first portion containing a first passageway having a diameter and defining a secondary valve sealing surface and having a second portion defining a second passageway having a diameter greater than said first passageway, a transitional inner wall between said first and second passageways defining a tapered primary valve sealing surface;

a second rigid tube member having an inner passageway defined therein and at least one first projection extending therefrom, said first and second tube members capable of mating engagement with axial alignment;

a cylindrical valve element having upper and lower portions and a top surface, said upper portion having a narrower diameter than said lower portion, a deformable shaped valve shoulder defined between said upper and lower portions, at least one annular deformable flange disposed proximate to said top surface, said at least one flange and said upper portion of said valve element being slidingly receivable within said first passageway such that said at least one flange deformably engages said secondary valve sealing surface; and a plurality of elastic members extending from said lower portion of said valve element such that when assembled said elastic members are maintained in elastic deformable engagement with said second tube member, whereby said shoulder of said valve element is capable of being releasably maintained in compressive engagement with said valve sealing surface by said elastic members so as to prevent passage of fluid therethrough.

2. The fluid control valve of claim 1, wherein said shoulder is rounded.

3. The fluid control valve of claim 1, further comprising means associated with said top surface of said upper portion for forming a fluid passageway between said top surface and a male luer connector tip capable of engaging said first tube member, said means comprising at least one second projection extending upward from said top surface.

4. The fluid control valve of claim 1, wherein said at least one flange is beveled.

5. The fluid control valve of claim 1, wherein said upper portion of said valve element is made of a material having a higher density than said lower portion of said valve element.

6. The fluid control valve of claim 1, wherein each of said plurality of elastic members comprises a segment of an elastomeric material, each end of which is associated with said valve element so as to form a loop.

7. The fluid control valve of claim 1, wherein said at least one first projection comprises at least one post.

8. The fluid control valve of claim 7, wherein said post extends upwardly from said inner wall of said inner passageway of said second tube member.

9. The fluid control valve of claim 1, wherein said second tube member has a male luer fitting associated therewith.

10. The fluid control valve of claim 1, wherein said second tube member is adapted to be integrally connected to a Y-site connector.

11. The fluid control valve of claim 1, wherein a plurality of said valve assemblies are adapted to be integrally connected by said second tube members to a manifold having an inlet end and an outlet end.

12. The fluid control valve of claim 1, wherein said second tube member is adapted to be integrally connected to a tube.

13. The fluid control valve of claim 1, wherein said elastic members maintain said valve element in an axially centered position within said first and second tube members.

14. The fluid control valve of claim 1, wherein said top surface of said valve element is generally even with said top of said first tube member when said shoulder is in compressive engagement with said primary valve sealing surface.

15. An automatic fluid control valve, comprising:

a first rigid tube member having a first portion containing a top and a first passageway defining a secondary valve sealing surface and having a second portion defining a second passageway having a diameter greater than said first passageway, a transitional inner wall between said first and second passageways defining a tapered primary valve sealing surface;

a second rigid tube member having an inner passageway defined therein, said first and second tube members capable of mating engagement with axial alignment;

a cylindrical valve element having upper and lower portions and a top surface, said upper portion having a narrower diameter than said lower portion, a deformable shaped valve shoulder defined between said upper and lower portions capable of sealingly engaging said primary valve sealing surface, at least one annular flange disposed about said upper portion of said valve element capable of sealingly engaging said secondary valve sealing surface so as to prevent fluid from passing therebetween, said top surface being engagable by a connector, said connector being capable of exerting a downward force on said valve element so as to release said seal between said valve shoulder and said primary valve sealing surface to permit fluid to pass therethrough, while said upper portion of said valve element maintains said at least one secondary valve seal and being slidingly receivable within said secondary valve sealing surface of said first passageway;

a plurality of elastic members extending from said lower portion of said valve element; and means associated with said second tube member for retaining said elastic members in elastomeric engagement with said second tube member said means comprising at least one first projection extending from said second tube member, whereby said valve shoulder is capable of being maintained in compressive engagement with said primary valve sealing surface by said elastic members so as to prevent passage of fluid therethrough when said valve element is not engaged by said connector.

16. The fluid control valve of claim 15, wherein when said fluid valve is in a closed position said top surface of said valve element is generally even with said top end of said first tube member.

17. The fluid control valve of claim 15, wherein said shoulder is rounded.

18. The fluid control valve of claim 15, further comprising means associated with said top surface of said upper portion for forming a fluid passageway between said top surface and a male luer connector tip capable of engaging said first tube member, said means comprising at least one second projection extending from said top surface.

19. The fluid control valve of claim 15, wherein said at least one flange is beveled.

20. The fluid control valve of claim 15, wherein said upper portion of said valve element is made of a material having a higher density than said lower portion of said valve element.

21. The fluid control valve of claim 15, wherein said second tube member has a male luer fitting associated therewith.

22. The fluid control valve of claim 15, wherein said second tube member is adapted to be integrally connected to a Y-site connector.

23. The fluid control valve of claim 15, wherein a plurality of said valve assemblies are adapted to be integrally connected by said second tube members to a manifold having an inlet end and an outlet end.

24. The fluid control valve of claim 15, wherein said second tube member is adapted to be integrally connected to a tube.

25. The fluid control valve of claim 15, wherein said elastic members maintain said valve element in an axially centered position within said first and second tube members.

26. A fluid control valve, comprising:

a first rigid tube member having a first portion containing a top and a first passageway having a diameter and defining a secondary valve sealing surface and having a second portion defining a second passageway having a diameter greater than said first passageway, a transitional wall between said first and second passageways defining a tapered primary valve sealing surface;

a second rigid tube member having an inner passageway defined therein and a top end and bottom end, said first and second tube members capable of mating engagement with axial alignment so as to form a fluid path therethrough;

a cylindrical valve element comprising
an upper portion terminating in a top surface and a lower portion, said lower portion having a larger diameter than said upper portion, a deformable shaped shoulder being defined between said upper and lower portions,
at least one deformable beveled annular flange disposed about said upper portion of said valve element capable of sealingly engaging said secondary valve sealing surface so as to prevent fluid from passing therebetween, and
a plurality of resilient deformable elastic members each elastic member comprising a segment of an elastomeric material, each end of said segment being associated with said lower portion of said valve seal member so as to form a loop;

means associated with said second tube member for retaining each of said loops comprising a plurality of posts extending from the inner wall of said inner passageway said elastic members maintaining said valve shoulder in releasably compressive engagement with said primary valve sealing surface; and means associated with said top surface of said upper portion for forming at least one fluid passageway between said top surface and a male luer connector capable of engaging said first tube member, said means comprising at least one projection extending from said top surface, whereby when said valve element is in a closed position said valve shoulder is maintained in compressive engagement against said primary valve sealing surface and said at least one flange sealingly engages said secondary valve sealing surface, and when said valve element is in an intermediate position said connector is partially engaged against said top surface and forced downward said valve element is urged downward against said tension created by said elastic members, thereby releasing said seal between said valve shoulder and said primary valve sealing surface, and when said valve element is in an open position said connector is fully engaged with said first tube member and said at least one flange enters said second passageway disengaging said secondary sealing surface and permitting passage of fluid between said first and said second tube members.

27. The fluid control valve of claim 26, wherein said elastic members maintain said valve element in an axially centered position within said first and second tube members.

28. The fluid control valve of claim 26, wherein said top surface of said valve element is generally even with said top of said first tube member when said shoulder is in compressive engagement with said primary valve sealing surface.

29. An automatic fluid control valve, comprising:

a first rigid tube member having a first portion defining a top and a first passageway having a diameter and defining a secondary valve sealing surface and having a second portion defining a second passageway having a diameter greater than said first passageway, a transitional inner surface between said first and second passageways defining a tapered primary valve sealing surface;

a second rigid tube member having an inner passageway defined therein, said first and second tube members capable of mating engagement with axial alignment;

a cylindrical valve element having upper and lower portions and a top surface, said upper portion having a narrower diameter than said lower portion and a bore extending from said top surface, a shaped valve shoulder defined between said upper and lower portions capable of sealingly engaging said primary valve sealing surface, at least one flange extending circumferentially around said upper portion, said at least one flange also extending partially inward over said top surface forming an annular undercut slot, said upper portion of said valve element providing at least one secondary valve seal and being slidingly receivable within secondary valve sealing surface of said first passageway;

a plurality of elastic members extending from said lower portion of said valve element; and means associated with said second tube member for retaining said elastic members in elastomeric engagement with said second tube member comprising a plurality of first projections extending from said inner passageway;

a cap comprising a stud capable of frictionally engaging said bore, a head having a flat surface and having a first edge having a diameter substantially similar to the diameter of said inward portion of said flange and a second edge having a diameter larger than said first edge, said flat surface having a plurality of second projections extending therefrom capable of forming fluid passageways when placed in contact with a connecting tube, whereby said shoulder of said valve element is capable of being maintained in compressive engagement with said valve sealing surface by said elastic members so as to prevent passage of fluid therethrough when said valve element is not engaged by connector.

30. The fluid control valve of claim 29, wherein said elastic members maintain said valve element in an axially centered position within said first and second tube members.

31. The fluid control valve of claim 29, wherein said top surface of said valve element is generally even with said top of said first tube member when said shoulder is in compressive engagement with said primary valve sealing surface.

32. An automatic fluid control valve, comprising:

a first rigid tube member having a first portion defining a top and a first passageway having a diameter and defining a secondary valve sealing surface and having a second portion defining a second passageway having a diameter greater than said first passageway, the transitional inner surface between said first and second passageways defining a tapered primary valve sealing surface;

a second rigid tube member having an inner passageway defined therein, said first and second tube members capable of mating engagement with axial alignment;

a cylindrical valve element having upper and lower portions and a top surface, said upper portion having a narrower diameter than said lower portion and a bore extending from said top surface, a shaped valve shoulder defined between said upper and lower portions capable of sealingly engaging said primary valve sealing surface, at least one flange extending circumferentially around said upper portion said at least one flange also extending above said top surface forming a recess having a diameter, said at least one flange being slidingly receivable in sealing engagement within secondary valve sealing surface of said first passageway;

a plurality of elastic members extending from said lower portion of said valve element;

means associated with said second tube member for retaining said elastic members in elastomeric engagement with said second tube member comprising a plurality of first projections extending from said inner passageway; and a cap comprising a stud capable of frictionally engaging said bore, said stud having at least one tapering barb projecting annularly therefrom, a disk-shaped head having a flat surface and a first edge having a diameter substantially similar to the diameter of said recess, said flat surface having a plurality of second projections extending therefrom capable of forming fluid passageways when placed in contact with a connecting tube.

33. The fluid control valve of claim 32, wherein said elastic members maintain said valve element in an axially centered position within said first and second tube members.

34. The fluid control valve of claim 32, wherein said top surface of said valve element is generally even with said top of said first tube member when said shoulder is in compressive engagement with said primary valve sealing surface.

* * * * *